US009776161B2

(12) United States Patent
Igney et al.

(10) Patent No.: US 9,776,161 B2
(45) Date of Patent: Oct. 3, 2017

(54) METHOD AND ARRANGEMENT FOR GENERATING NITRIC OXIDE

(75) Inventors: Claudia Hannelore Igney, Erlangen (DE); Rainer Hilbig, Aachen (DE); Achim Gerhard Rolf Koerber, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 474 days.

(21) Appl. No.: 13/988,786

(22) PCT Filed: Nov. 28, 2011

(86) PCT No.: PCT/IB2011/055347
§ 371 (c)(1),
(2), (4) Date: Jul. 1, 2014

(87) PCT Pub. No.: WO2012/073185
PCT Pub. Date: Jun. 7, 2012

(65) Prior Publication Data
US 2015/0053544 A1   Feb. 26, 2015

(30) Foreign Application Priority Data
Dec. 3, 2010 (EP) .................... 10193578

(51) Int. Cl.
*B01J 19/12*   (2006.01)
*C01B 21/24*   (2006.01)
(Continued)

(52) U.S. Cl.
CPC ............ *B01J 19/12* (2013.01); *A61K 33/00* (2013.01); *A61M 16/10* (2013.01); *C01B 21/24* (2013.01);
(Continued)

(58) Field of Classification Search
CPC  B01J 19/12; B01J 2219/0877; B01J 2219/12; C01B 21/24; A61K 33/00;
(Continued)

(56) References Cited

U.S. PATENT DOCUMENTS 1,334,590 A * 3/1920 Bloom .................... C01B 21/30
204/157.46
2,134,206 A * 10/1938 Roberts ................. C01B 21/203
204/157.46
(Continued)

FOREIGN PATENT DOCUMENTS

CN      1730115 A    2/2006
EP      1630133      3/2006
(Continued)

*Primary Examiner* — Keith Hendricks
*Assistant Examiner* — Colleen M Raphael
(74) *Attorney, Agent, or Firm* — Michael W Haas

(57) ABSTRACT

The present invention relates to a method for generating nitric oxide, which comprises the steps of: providing a precursor solution comprising a nitric oxide precursor in a first reservoir (12), guiding the precursor solution through a reaction chamber (16), thereby subjecting the precursor solution to radiation to generate nitric oxide, guiding the generated nitric oxide out of the reaction chamber (16) by a stream of carrier gas, and guiding the reacted solution into a second reservoir (14). The method according to the invention provides a method of generating nitric oxide, or a flow of nitric oxide comprising gas, in which the concentration of the nitric oxide may be kept especially constant. Also claimed is an apparatus for generating nitric oxide comprising reservoirs for the precursor solution and the reacted solution and a reaction chamber.

13 Claims, 4 Drawing Sheets

(51) Int. Cl.
*A61M 16/10* (2006.01)
*A61K 33/00* (2006.01)

(52) U.S. Cl.
CPC ............. *A61M 2016/1035* (2013.01); *A61M 2202/0275* (2013.01); *B01J 2219/0877* (2013.01); *B01J 2219/12* (2013.01)

(58) Field of Classification Search
CPC .......... A61M 16/10; A61M 2202/0275; A61M 2016/1035
USPC .............................. 204/157.46, 157.44, 157.5
See application file for complete search history.

(56) References Cited

U.S. PATENT DOCUMENTS

| | | | |
|---|---|---|---|
| 2,898,277 A * | 8/1959 | Paul | C01B 21/20 204/157.46 |
| 3,378,475 A * | 4/1968 | Morse | B01J 19/081 204/157.46 |
| 3,663,167 A | 5/1972 | De Vry | |
| 3,840,342 A * | 10/1974 | Neti | C01B 21/262 204/157.46 |
| 4,167,463 A * | 9/1979 | Conrad | B01J 19/121 204/157.46 |
| 5,094,815 A | 3/1992 | Conbov et al. | |
| 5,485,827 A | 1/1996 | Zapol | |
| 2003/0062043 A1* | 4/2003 | Fine | A61K 9/007 128/203.12 |
| 2003/0064028 A1 | 4/2003 | Fine et al. | |
| 2007/0190184 A1 | 8/2007 | Montgomery et al. | |
| 2009/0191284 A1* | 7/2009 | Conoci | B01J 19/123 204/157.46 |
| 2010/0108489 A1* | 5/2010 | Andersen | B01J 19/123 204/157.46 |

FOREIGN PATENT DOCUMENTS

| | | |
|---|---|---|
| EP | 1903003 | 3/2008 |
| WO | WO9420415 A1 | 9/1994 |

* cited by examiner

METHOD AND ARRANGEMENT FOR GENERATING NITRIC OXIDE

FIELD OF THE INVENTION

The invention relates to the field of nitric oxide generation. More particularly, the invention relates to the field of nitric oxide generation for therapeutic applications.

BACKGROUND OF THE INVENTION

It is widely known to use nitric oxide (NO) in a variety of applications. Next to technical applications such as an intermediate in the Ostwald process for the synthesis of nitric acid from ammonia, especially several therapeutic applications using nitric oxide are known.

One of the most famous therapeutic applications of nitric oxide is the administration for neonates suffering from Persistent Pulmonary Hypertension (PPHN). However, many comparable or other therapeutic applications are known and discussed for the use of nitric oxide. As an example, nitric oxide is used by the endothelium of blood vessels to signal the surrounding smooth muscle to relax, thus resulting in widening the blood vessels and therefore increasing blood flow. This leads to nitric oxide being particularly applicable for the therapy of hypertension. Further exemplary applications for nitric oxide are directed towards improving lung function and treating or preventing bronchoconstriction, reversible pulmonary vasoconstriction, for treating or preventing arterial restenosis resulting from excessive intimal hyperplasia, or for treating chronic obstructive pulmonary disease (COPD). Apart from that, the administration of nitric oxide is particularly useful for treatment of infected tissue e.g. to kill bacteria. This application mostly involves topical delivery of a source of nitric oxide containing gas to a skin surface containing infected tissue.

The storage of nitric oxide for example in containers, or gas cylinders, respectively, may however cause difficulties. Due to the fact that nitric oxide tends to react with oxygen, even minor impurities of oxygen in the stored gas may cause the formation of nitrogen oxides in higher oxidation states, in particular the formation of toxic nitrogen dioxide ($NO_2$). Therefore, nitric oxide has only limited useful life time and may thus be stored only in a low concentration and for a limited time. For many applications, it is therefore preferred to generate nitric oxide in situ, i.e. directly before use.

The generation of nitric oxide may additionally lead to problems because of which several attempts to form nitric oxide are exercised.

Known from EP 1 903 003 A1 is a method and an arrangement for generating nitric oxide. According to this method, nitric oxide is generated by a photolytic cleavage of nitrite ions being present in a nitrite containing aqueous solution. In detail, an aqueous nitrite solution further comprising antioxidants is guided in a reaction chamber in which it is subjected to electromagnetic radiation for a defined period of time. Due to the influence of the radiation, the nitrite ion is cleaved, wherein nitric oxide is generated. The so generated nitric oxide may then be transported out of the reaction chamber by means of a carrier gas.

One of the major drawbacks of this known method for generating nitric oxide is the fact that under some circumstances, the concentration of the formed nitric oxide may not be kept completely constant over a long period of time.

SUMMARY OF THE INVENTION

It is an object of the invention to provide a method and an arrangement for generating nitric oxide in which the concentration of the generated nitric oxide may be kept constant in definite ranges over a long period of time.

This object is achieved by a method according to claim 1 and by an arrangement according to claim 10. Preferred embodiments are defined in the dependent claims.

The present invention relates to a method for generating nitric oxide, which comprises the steps of: providing a precursor solution comprising a nitric oxide precursor in a first reservoir, guiding the precursor solution through a reaction chamber, thereby subjecting the precursor to radiation to generate nitric oxide, guiding the generated nitric oxide out of the reaction chamber by a stream of carrier gas, and guiding the reacted solution into a second reservoir.

According to the invention, a nitric oxide precursor shall mean a substance which may react under release of nitric oxide. In particular, the precursor is capable of releasing nitric oxide by subjecting the latter to radiation, especially to electromagnetic radiation. A nitric oxide precursor may thus comprise a substance or a mixture of substances releasing nitric oxide. Additionally, the nitric oxide precursor may comprise additives which support the release of nitric oxide from a substance, or a mixture of substances. Examples for these kinds of additives comprise in a non limiting manner a catalyst, an enzyme, a photoacceptor, or a photoamplifier. Furthermore, the nitric oxide precursor may comprise a subtance or a mixture of substances which release nitric oxide due to a chemical reaction, for example.

The nitric oxide prescursor is provided in form of a solution in the first reservoir. It may be filled in that reservoir directly before use, or it may be stored in that reservoir for a defined time in order to allow the generation of nitric oxide to start spontaneously and without any essential prearrangements. Consequently, the first reservoir may be impermeable for any kind of radiation in order to prevent the nitric oxide precursor to react, or to age.

In order to start the nitric oxide generation, the precursor solution is guided into a reaction chamber and through the latter, thereby subjecting the solution, or the precursor, respectively, to defined radiation, particularly to electromagnetic radiation. The radiation then starts a photolysis process resulting in the nitric oxide precursor to release nitric oxide.

The reacted solution is then guided to a second reservoir, whereas the generated nitric oxide may be removed from the reaction chamber by means of a stream of carrier gas.

Due to the fact that the solution is guided from the first reservoir through the reaction chamber and into the second reservoir, the solution inside the reaction chamber is changed constantly. This allows to always subject fresh precursor solution to radiation. Consequently, the concentration of the nitric oxide precursor inside the reaction chamber may be kept constant or at least substantially constant. In case the remaining reaction parameters are kept constant as well, the concentration of the nitric oxide to be generated is kept constant in the carrier gas throughout the whole reaction time. Accordingly, the nitric oxide stream which may be formed has a constant composition from the start of the reaction until the end of the reaction, i.e. until all of the precursor solution is guided into the second reservoir.

In case the first reservoir is completely emptied, the latter may be exchanged and a new reaction cycle may follow.

According to the invention it is thus possible to generate nitric oxide under constant conditions allowing a stream of nitric oxide comprising gas to be formed to have a constant composition. Furthermore, the concentration of the nitric oxide may by tailored in a very exact way to the desired application, for example by adjusting the flow of carrier gas, the flow of precursor solution as well as by adjusting the power of the radiation source.

Due to this flexibility and the constant generated nitric oxide flow, the method according to the invention is particularly suitable for therapeutic applications. In this case, it is especially important to have a well defined and constant concentration of nitric oxide in order to get the desired therapeutic effects without any danger for the patient.

According to a preferred embodiment of the present invention, the precursor solution is guided through the reaction chamber with a constant flow. This embodiment enables to have constant reaction conditions at every stage of the reaction. The reacted solution is directly guided to the second reservoir, wherein fresh precursor solution comprising fresh nitric oxide precursor in a defined concentration is guided into the reaction chamber. Consequently, no adjustments have to be carried out, all parameters may be kept constant.

In an alternative preferred embodiment, the precursor solution is guided through the reaction chamber intermittently. According to the invention, this shall mean that the reaction chamber is filled with a defined amount of precursor solution. The latter is subjected to radiation, wherein the concentration of the nitric oxide precursor is slowly decreasing. In order to get essentially constant concentrations of the generated nitric oxide, particularly in the gas stream downstream the reaction chamber, after a certain amount of time the reacted solution is guided into the second reservoir, wherein in turn fresh precursor solution is guided from the first reservoir into the reaction chamber. Then, a new reaction may start thereby subjecting the precursor solution, or the precursor, respectively, with radiation. This allows keeping the concentration within defined ranges.

According to a further preferred embodiment of the present invention, the reacted solution is recirculated to the first reservoir. According to this embodiment, it is utilized that dowmstream the reaction chamber, still an amount, even a major amount, of the nitric oxide precursor is present in the reacted solution. The reacted solution shall thereby particularly mean the solution leaving the reaction chamber. Consequently, it is not necessary to discard that solution, but it may be reused instead. In detail, the reacted solution may be guided through the reaction chamber again to subject the remaining precursor to radiation, thereby forming nitric oxide. Due to the fact that the concentration of the nitric oxide precursor is lower compared to the first run, but it is again constant during its passage through the reaction chamber, again, a constant flow of nitric oxide may be generated. In order to get the desired concentration, one or a plurality of reaction parameters may be adjusted.

Consequently, this embodiment allows an especially economic way of generating nitric oxide, as no valuable precursor solution is discarded, but it may be reused again.

According to a further embodiment of the present invention, further precursor is added to the reacted solution. This embodiment allows to provide precursor solution in the first reservoir at a second run, for example, having the same concentration of nitric oxide precursor compared to the first run. Consequently, all reaction parameters may be kept constant, thereby allowing a constant flow of nitric oxide to be formed. It is just necessary to add the amount of nitric oxide precursor which has reacted to release nitric oxide. Consequently, a constant flow of nitric oxide may be generated for an essentially unlimited time range, thereby being very cost-saving.

According to a still further embodiment of the present invention, at least one reaction parameter is controlled in response to the nitric oxide concentration downstream the reaction chamber. This is an especially secure way to react in response to a potentially changed concentration of the nitric oxide concentration. In detail, if the concentration of nitric oxide in the generated nitric oxide comprising gas runs out of a defined, or predefined range, the reaction parameters may be adjusted in order to get the desired concentration again. In detail, reaction parameters which may be adjusted, comprise in a non-limiting manner: flow of carier gas, flow and/or reaction time of the precursor solution, concentration of the precursor, power of the radiation source, etc. Consequently, according to this embodiment, a flow having a constant composition is further ensured during the whole reaction time.

It is furthermore preferred that an antioxidant is added to the precursor solution. According to the invention, an antioxidant shall mean a compound which is capable of decomposing or neutralizing reactive nitrogen oxide species (RON), for example $NO_2$-radicals, or reactive oxygen species (ROS). Especially preferred examples comprise in a non-limiting manner ascorbic acid, ascorbate, vitamine E and its derivatives, thiols, radical scavengers oder ROS und/oder RNS decomposing enzymes.

By adding antioxidants like described above, the formation of reactive intermediate products as well as the formation of nitrogen dioxide is prevented or at least decreased. Additionally, if these compounds are anyhow formed, the latter will be decomposed again. Consequently, especially with respect to the toxic nitrogen dioxide, the latter is not present in the reacted solution, or it is present in such a minor amount, that it will stay in the solution. In contrast thereto, the presence of nitrogen dioxide, for example, in the produced flow of nitric oxide coprising gas is securely prevented. Thereby, the generation of nitric oxide is not hindered, allowing the purity if the generated gas to be increased. This embodiment is thus especially preferred in case the generated nitric oxide, or the nitric oxide comprising gas, respectively, is used for therapeutical, or cosmetical applications.

With respect to the precursor solution, it is preferred that an aqueous nitrite solution is used as precursor solution, in particular a sodium nitrite solution. Nitrite solutions are non toxic and may be disposed without problems. Additionally, a nitrite solution may be stored over a substantially unlimited time without side reactions to occur. Consequently, this solution may be stored in the first reservoir and the reaction may be started when appropriate.

In a further preferred embodiment of the present invention, the precursor is subjected to radiation in the range of ≥320 nm to ≤440 nm. This kind of radiation, lying in the range of UV-radiation, may be handled without problems, leading to the method according to the invention to be performed in a save manner. Additionally, such radiation is very well suited for releasing nitric oxide from a plurality of suitable nitric oxide precursors, for example from a nitrite.

The present invention further relates to an arrangement for generating nitric oxide, comprising a first reservoir for receiving a precursor solution comprising a nitric oxide precursor, a reaction chamber being in communication with a radiation source for subjecting the precursor solution with radiation in the reaction chamber and being in fluid communication with the first reservoir, a second reservoir for receiving reacted solution being in fluid communication with the reaction chamber, and a gas inlet and a gas outlet for guiding a carrier gas through the reaction chamber.

Such an arrangement is designed for carrying out a method for generating nitric oxide like described above, leading to the above defined advantages.

Additionally, the arrangement according to the invention may be designed in a very compact manner. Consequently, the arrangement according to the invention may be used in a stationary manner, as well as a portable device. In detail, the arrangement according to the invention may be used as a homecare device for therapeutic applications.

The service and the handling of a device comprising the arrangement according to the invention is furthermore very easy. For example, the first reservoir as well as the second reservoir may be arranged in a detachable way. This enables these components to be removable articles. With respect to the first reservoir, the letter may be provided filled with nitric oxide precursor solution, and may be discarded in case all of the solution was reacted. In this case, the first reservoir may be disconnected, removed and exchanged. Accordingly, the second reservoir may be removed from the remaining arrangement in case it is full and it may be emitted, or removed afterwards.

According to a preferred embodiment of the arrangement according to the invention, a gas reservoir is provided downstream the reaction chamber. This embodiment is especially preferred in case the arrangement is used with intermittently, i.e. discontinous and with a pulsed flow of solution. In this case, a discontinuous flow of nitric oxide, or nitric oxide comprising gas, respectively, will be generated directly after the reaction chamber. Due to the provision of a gas reservoir downstream the reaction chamber, the nitric oxide comprising gas may be stored allowing a continuos flow of nitric oxide comprising gas to be formed even in case the reaction as such is performed in an intermittent way.

According to a still further preferred embodiment of the arrangement according to the invention, a recirculation loop is provided for guiding the reacted solution back to the first reservoir. This allows recirculating the reacted solution back to the first reservoir and thus saving nitric oxide precursor. Consequently, an arrangement according to this embodiment of the present invention may be utilized in an especially economic way. In this case the second reservoir may be formed solely by the recirculation loop connecting the first reservoir and the reaction chamber, or an additional recirculation loop may be provided downstream the second reservoir.

With this regard, it is especially preferred that a third reservoir for receiving precursor solution is provided in fluid communication with the recirculation loop, the first reservoir and/or the second reservoir. This allows adding fresh nitric oxide precursor to the reacted solution and thus ensuring that the concentration of the nitric oxide precursor in the first reservoir is kept constant during every stage of the reaction. The third reservoir may thereby be provided inside the recirculation loop, the first reservoir and/or the second reservoir. However, it is mostly preferred that the third reservoir is attached to the outer wall, or casing, of the recirculation loop, the first reservoir, and/or the second reservoir. In this case, the third reservoir may easily be exchanged in case all of the precursor was used.

According to a still further preferred embodiment of the arrangement according to the invention, a nitric oxide detector is provided downstream the reaction chamber. This allows to directly react to changed nitric oxide concentrations, for example, in order to ensure the nitric oxide concentration as well as the composition of the generated gas to be kept constant.

With this regard, it is especially preferred, that a control unit is provided for adjusting at least one reaction parameter according to the nitric oxide concentration downstream the reaction chamber. According to this embodiment, a fully, or substantially fully automated method may be performed. In detail, reaction parameters which may be controlled by the control unit, may comprise in a non-limiting manner: flow of carrier gas, flow and/or reaction time of the precursor solution, concentration of the precursor, power of the radiation source, etc.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

In the following, different embodiments of the present invention are schematically shown in the respective figures, wherein the same or comparable components are referred to with the same reference signs.

Figure 1:
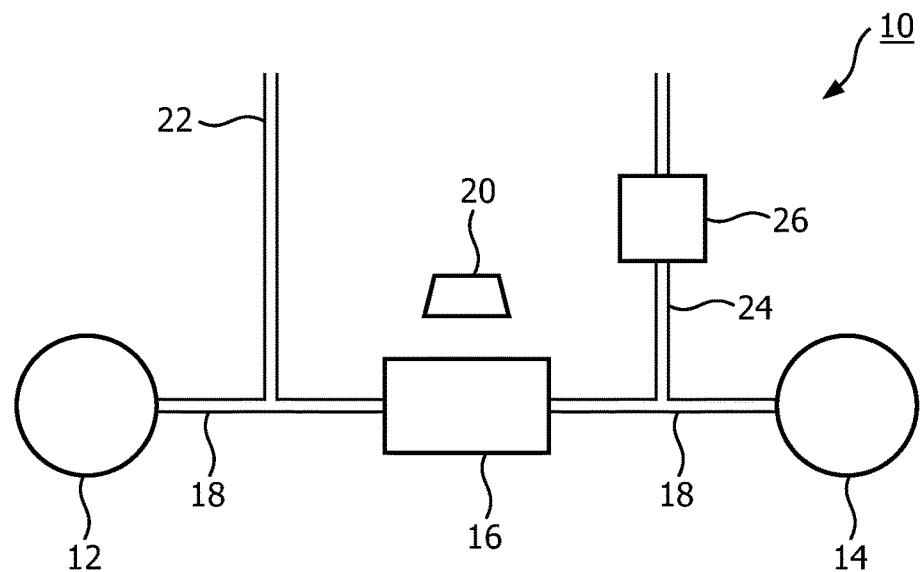
FIG. 1 shows a schematical view of an embodiment of an arrangement for generating nitric oxide according to the invention.

In FIG. 1, an arrangement 10 for generating nitric oxide is schematically shown. The arrangement 10 is particularly suitable for the generation of nitric oxide in therapeutic applications and with this regard, it is particularly suitable for portable home care devices.

The arrangement 10 according to the invention comprises a first reservoir 12 and a second reservoir 14. The first reservoir 12 is designed for receiving a precursor solution comprising a nitric oxide precursor, whereas the second reservoir 14 is designed for receiving reacted solution. The reservoirs 12, 14 may be formed in any shape appropriate and furthermore may be formed from every suitable material. For example, the reservoirs 12, 14 may be formed from glass, or plastics.

With respect to the precursor solution, the latter comprises a nitric oxide precursor, i.e. in particular a substance or a mixture of substances which is capable of releasing nitric oxide, especially due to an impact of radiation. Examples for nitric oxide precursors comprise in a non limiting manner S-, N- or O-nitrosated compounds, NO-metallic compounds, or NO-chelating compounds. However, especially preferred are organic or inorganic nitrites, especially an aqueous nitrite solution.

It is especially preferred that the nitric oxide precursors are present in an aqueous solution. This kind of solution is non toxic and my thus be stored and handled without problems. Suitable concentrations of the nitric oxide precursor lie in a range of $\geq 0.1$ mM to $\leq 10000$ mM, in particular in a range of ≥0.5 mM to ≤1500 mM. Additionally, further additives, such as antioxidants, may be added to the precursor solution.

Between the two reservoirs 12, 14, a reaction chamber 16 is provided, which may be connected to the first and second reservoir 12, 14 via a conduct 18 and thus being in fluid communication to the latter. The reaction chamber 16 is designed for subjecting precursor solution located therein to radiation. Consequently, it is most preferred that the reaction chamber 16 is formed from glass, for example from quartz glass. However, the reaction chamber 16 may be formed from any suitable material as long as it is at least partly permeable for the desired radiation.

In order to subject the reaction chamber 16, or the material located therein, with radiation, the reaction chamber 16 is in communication with a radiation source 20. This means that the radiation source 20 as well as the reaction chamber 16 are arranged to allow radiation to act on the inside of the reaction chamber 16. The radiation source 20 is designed for forming the desired radiation. For example, the radiation source 20 may be a UV-lamp for generating radiation in a range of ≥320 nm to ≤440 nm. Additionally, the radiation source may work with a power of ≤20 W, for example. In case a precursor solution is located in the reaction chamber 16 and the radiation source 20 is turned on, nitric oxide is formed in the reaction chamber 16 due to a release of nitric oxide from the precursor. In order to form a flow of nitric oxide comprising gas, the arrangement 10 comprises a gas inlet 22 and a gas outlet 24 for guiding a carrier gas through the reaction chamber 16. The gas inlet 22 is preferably located upstream the reaction chamber 16, whereas the gas outlet 24 is preferably located downstream the reaction chamber 16. Consequently, the generated nitric oxide may be removed from the reaction chamber 16 by the flow of the carrier gas, in particular an inert gas, like nitrogen.

In a preferred embodiment, the arrangement 10 comprises a gas reservoir 26 downstream the gas outlet 24 in order to generate a constant flow of generated gas in any case, like will be apparent down below.

Figure 2:
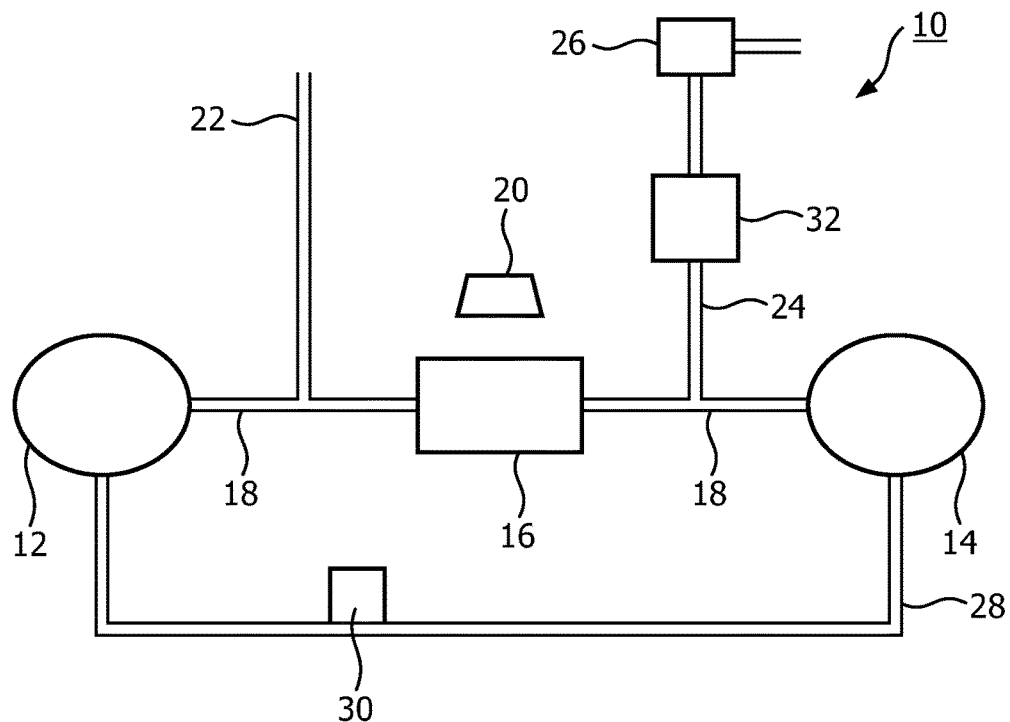
FIG. 2 shows a schematical view of a further embodiment of an arrangement for generating nitric oxide according to the invention.

A further embodiment of the present invention is shown in FIG. 2. This embodiment mainly corresponds to the embodiment according to FIG. 1, because of which it is referred to the above with respect to the components not described in detail here.

According to FIG. 2, the arrangement 10 further comprises a recirculation loop 28, which may connect the second reservoir 14 to the first reservoir 12. However, as the second reservoir 14 may not be strictly necessary in case a recirculation loop 28 is provided, the second reservoir 14 as such may be arranged in the form of a recirculation loop 28, or as a part of it. In the latter case, the recirculation loop 28 may connect the reaction chamber 16, or the conduct 18, directly to the first reservoir 12.

The recirculation loop 28 allows to recirculate the reacted solution back to the first reservoir 12 and thus to reuse it again. With this regard, a third reservoir 30 for receiving precursor solution may be provided in fluid communication to the recirculation loop 28, the first reservoir 12, or the second reservoir 14. Accordingly, the reacted precursor may be refilled, for example by adding, or injecting further precursor, or precursor solution, into the reacted solution, in order to provide a precursor solution in the first reservoir having always the same concentration of the nitric oxide precursor.

Additionally, it is preferred that the arrangement 10 comprises a nitric oxide detector 32 downstream the reaction chamber 16. The nitric oxide detector 32 may detect the exact concentration of the nitric oxide in the generated nitric oxide comprising gas and may thus give a notice in case the amount of nitric oxide to be formed decreases or falls out of a defined range. In this case, at least one reaction parameter may be adjusted in order to again receive the desired concentration of nitric oxide in the nitric oxide comprising gas. As an example, the power of the radiation source may be increased, or the concentration of the nitric oxide precursor may be increased.

With this regard, it is preferred that a control unit, not shown as such, is provided for controlling and adjusting the reaction parameters according to and in response to the nitric oxide concentration downstream the reaction chamber 16, or the gas outlet 24, respectively. Accordingly, the control unit may preferably be connected to each of the nitric oxide detector 32, the radiation source 20, and the third reservoir 30, or an injector of the latter, respectively.

In the following, different embodiments of the method for generating nitric oxide which may be performed with an arrangement like described above will be described. Generally, the method according to the invention comprises the following steps: providing a precursor solution comprising a nitric oxide precursor in a first reservoir, guiding the precursor solution through a reaction chamber, thereby subjecting the precursor solution to radiation to generate nitric oxide, guiding the generated nitric oxide out of the reaction chamber by a stream of carrier gas, and guiding the reacted solution into a second reservoir.

Figure 3:
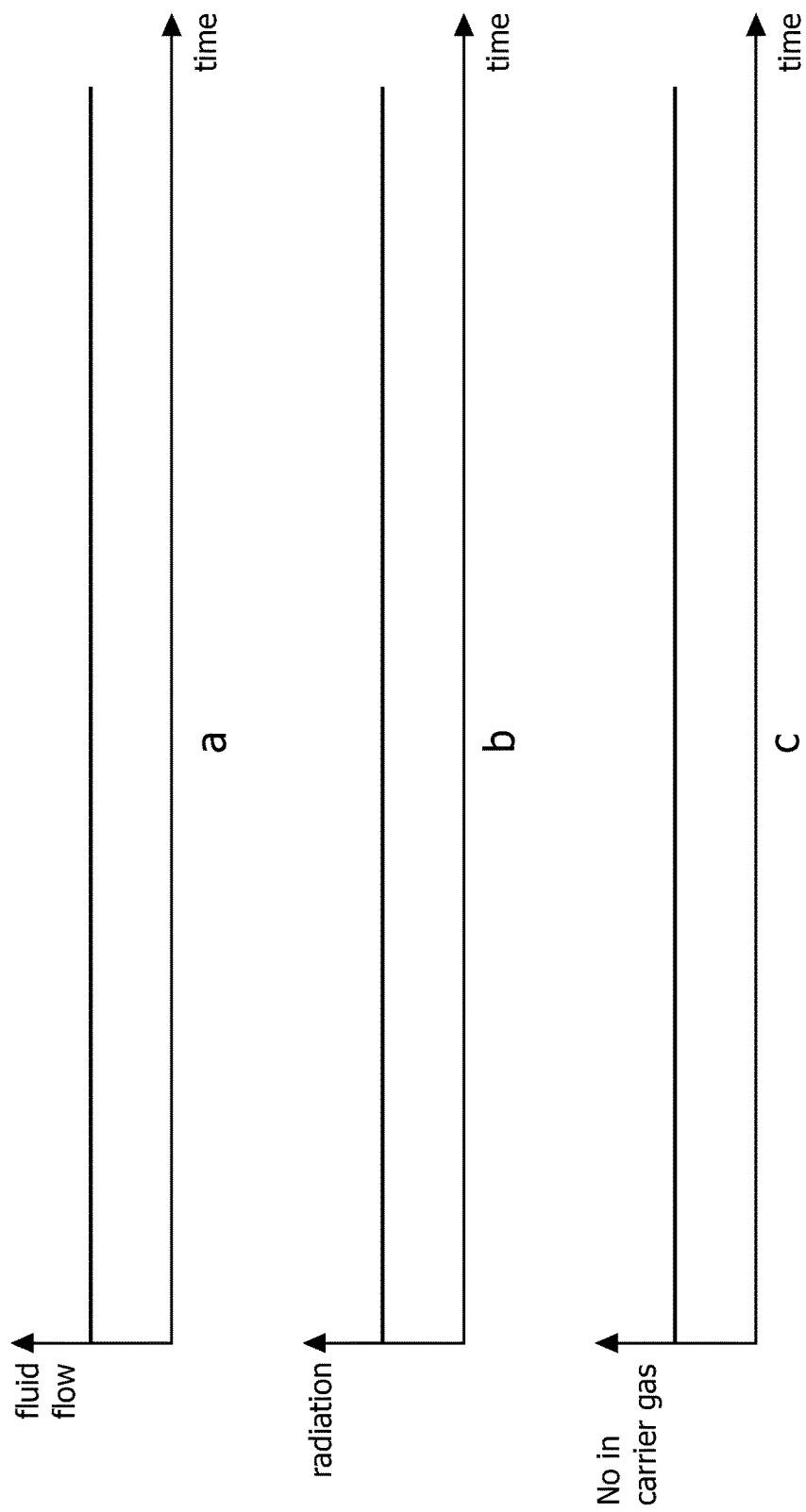
FIG. 3 shows schematic diagrams vizualizing an embodiment of the method for generating nitric oxide according to the invention.

According to FIG. 3, the precursor solution is guided through the reaction chamber 16 in a constant and continuous flow. This is visualized by the graph a), in which the amount of precursor solution, or fluid, flowing through the reaction chamber 16 is plotted against the time. Accordingly, the power of the radiation acting on the nitric oxide precursor is kept constant, which is visualized in graph b), in which the power of radiation is plotted against the time. The above chosen parameters result in the concentration of nitric oxide in the nitric oxide comprising gas being constant through the whole reaction time. This effect is visualized in graph c), in which the concentration of nitric oxide is plotted against the time.

Figure 4:
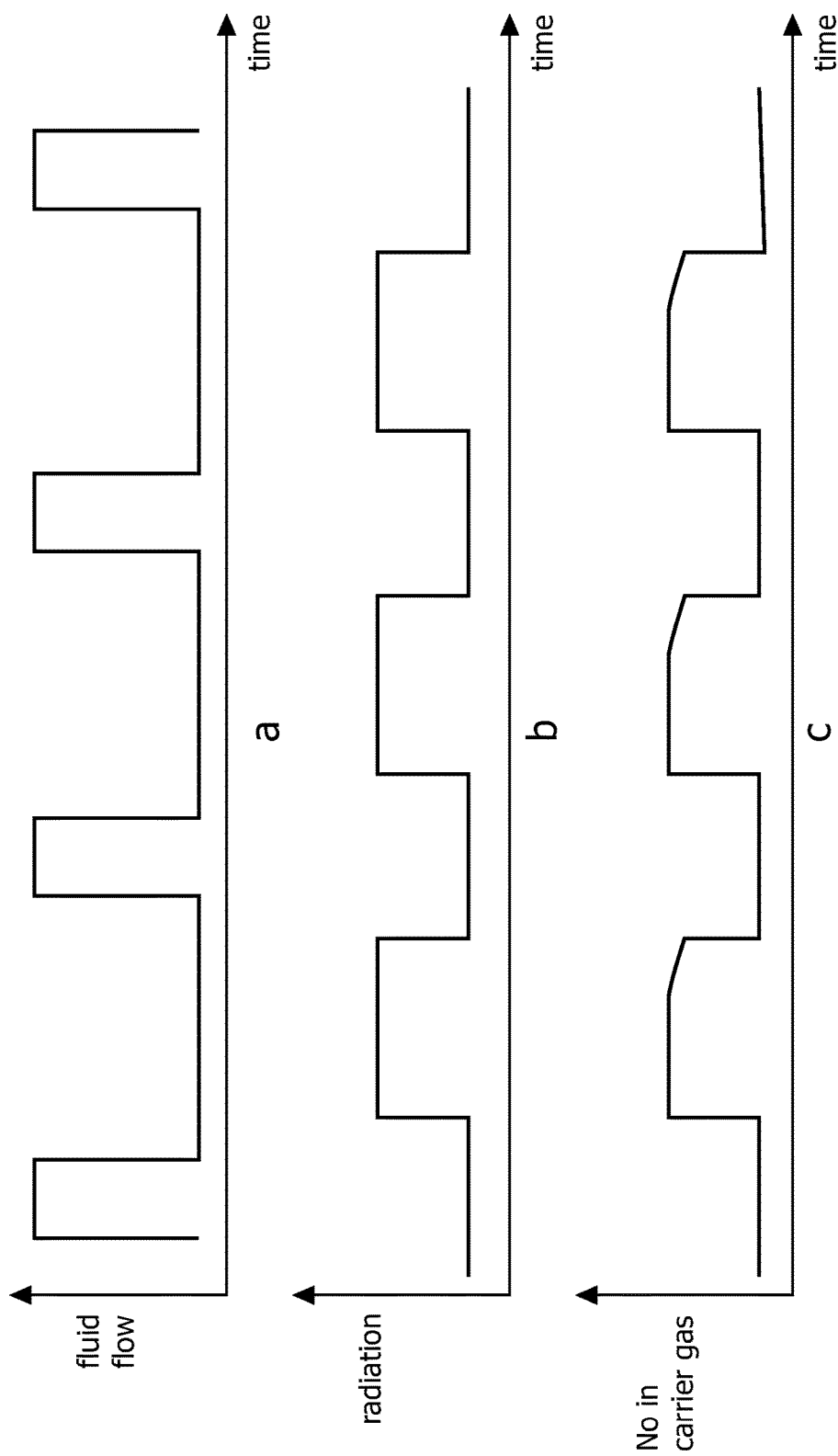
FIG. 4 shows schematic diagrams vizualizing a further embodiment of the method for generating nitric oxide according to the invention.

An alternative embodiment for performing a method according to the invention is shown in FIG. 4. According to FIG. 4, the precursor solution is guided through the reaction chamber 16 intermittently, or pulsed. This is visualized by graph a) of FIG. 4, in which the flow of precursor solution is plotted against the time. It can be seen, that the solution is pumped into the reaction chamber 16 in which it lasts for a certain reaction time. During this reaction time, the solution, or the precursor, is subjected to radiation, which is visualized by graph b) of FIG. 4, in which the power of radiation is plotted against the time. The above method results in the nitric oxide being generated during the reaction time, i.e. during the time in which the solution is subjected to radiation and no flow of solution is performed. This is shown in graph c) of FIG. 4, in which the concentration of nitric oxide is plotted against the time. It can be seen that the concentration is high during the radiation step. The concentration of nitric oxide starts directly after turning on the radiation source 20. However, the provision of a carrier gas may slightly decelerate the timing of the desired concentration in the gas phase. After a certain decade of radiation, the concentration of nitric oxide decreases, which may be explained by the decrease of precursor concentration which is due to the ongoing reaction. In case the nitric oxide concentration falls under a certain level, the radiation stops and the flow of solution is set to a certain level, thereby filing fresh solution into the reaction chamber 16. In this embodiment, it is preferred to use a gas reservoir 26 downstream the gas 24 outlet in order to get a constant and continuous flow of nitric oxide comprising gas.

Figure 5:
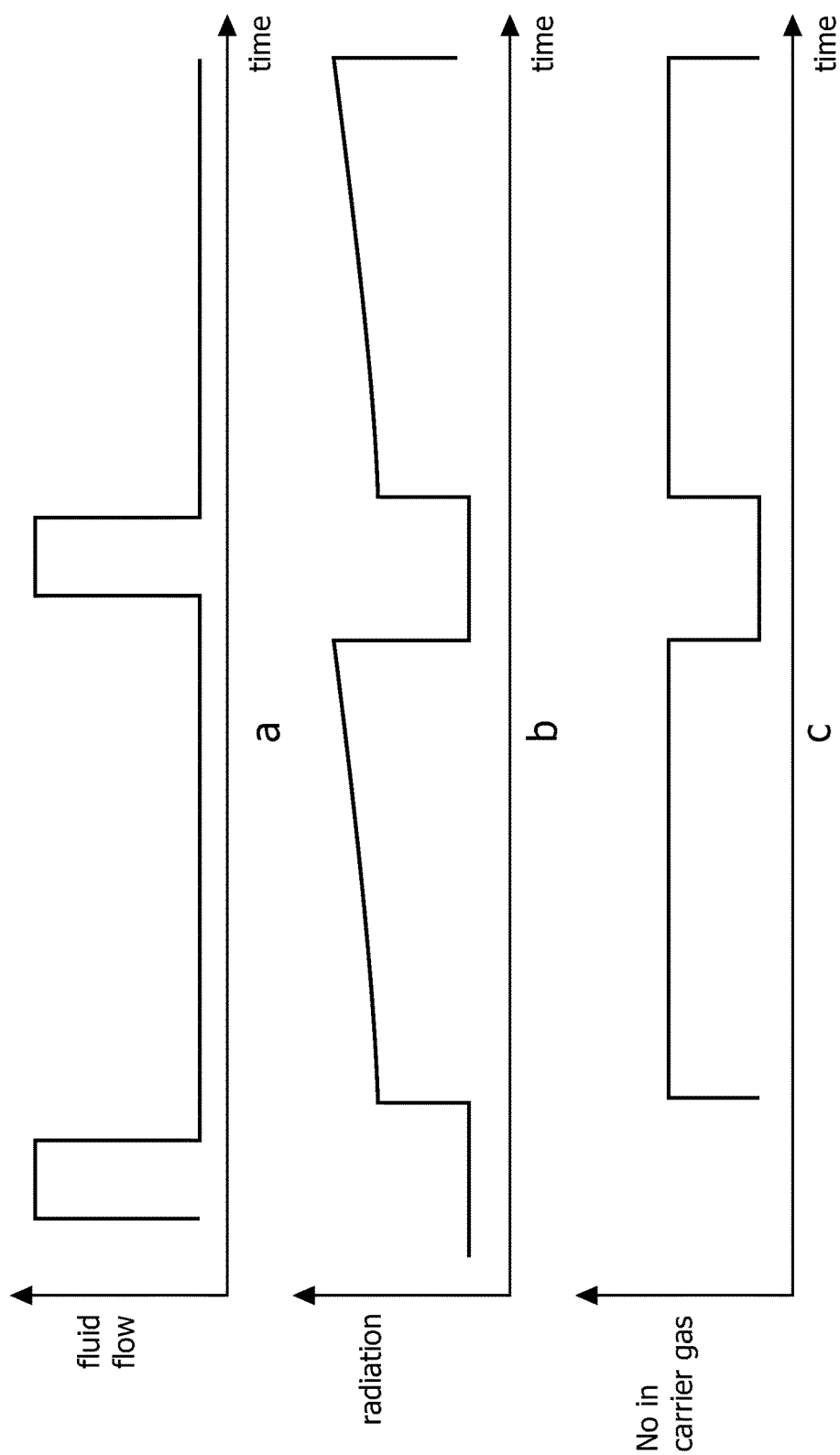
FIG. 5 shows schematic diagrams vizualizing a further embodiment of the method for generating nitric oxide according to the invention.

A still further embodiment of the method according to the invention is shown in FIG. 5. According to FIG. 5, again, an intermittent, or pulsed flow of precursor solution is guided into the reaction chamber 16, which is visualized by graph a) of FIG. 5, in which in which the flow of precursor solution is plotted against the time. Again, it can be seen, that the solution is pumped into the reaction chamber 16 in which it lasts for a certain reaction time. During this reaction time, the solution, or the precursor, is subjected to radiation, which is visualized by graph b) of FIG. 5, in which the power of radiation is plotted against the time. However, according to graph b) of FIG. 5, the intensity of the radiation source is slowly increased. This may be performed according to a predefined scheme, or according to the detected concentration of nitric oxide downstream the gas outlet 24, for example by the control unit. The increase of the radiation intensity results in the concentration of the nitric oxide to remain constant during the whole radiation step. This is shown in graph c) of FIG. 5, in which the concentration of nitric oxide is plotted against the time. In this embodiment, it is again preferred to use a gas reservoir 26 downstream the gas outlet 24 in order to get a constant and continuous flow of nitric oxide comprising gas.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. Method for generating nitric oxide, which comprises the steps of:
    providing a precursor solution comprising a nitric oxide precursor in a first reservoir,
    guiding the precursor solution through a reaction chamber, thereby subjecting the precursor solution to radiation to generate nitric oxide, wherein a concentration of the guided precursor solution is kept constant,
    guiding the generated nitric oxide out of the reaction chamber by a stream of carrier gas, and
    guiding the reacted solution into a second reservoir, wherein:
    in a first mode of operation, the precursor solution is continuously guided through the reaction chamber and a power of the radiation acting on the precursor solution is held at a constant level such that a concentration of generated nitric oxide in the carrier gas is substantially constant;
    in a second mode of operation, the precursor solution is pulsed through the reaction chamber, and the power of the radiation is correspondingly pulsed to the constant level, such that a concentration of nitric oxide in the carrier gas generated from an individual second mode pulse of precursor solution decreases with time; and
    in a third mode of operation, the precursor solution is pulsed through the reaction chamber, and the power of the radiation is correspondingly increased over time for an individual third mode pulse of precursor solution, such that the concentration of nitric oxide in the carrier gas generated from the individual third mode pulse of precursor solution is constant over time.

2. Method according to claim 1, wherein the reacted solution is recirculated to the first reservoir.

3. Method according to claim 2, wherein further precursor is added to the reacted solution.

4. Method according to claim 1, wherein at least one reaction parameter is controlled in response to the nitric oxide concentration downstream from the reaction chamber.

5. Method according to claim 1, wherein an antioxidant is added to the precursor solution.

6. Method according to claim 1, wherein an aqueous nitrite solution is used as the precursor solution.

7. Method according to claim 1, wherein the precursor is subjected to radiation in the range of $\geq 320$nm to $\leq 440$nm.

8. Apparatus for generating nitric oxide, comprising
    a first reservoir for receiving a precursor solution comprising a nitric oxide precursor,
    a reaction chamber being in communication with a radiation source for subjecting the precursor solution with radiation in the reaction chamber and being in fluid communication with the first reservoir,
    a second reservoir for receiving reacted solution being in fluid communication with the reaction chamber, and
    a gas inlet and a gas outlet for guiding a carrier gas through the reaction chamber, wherein the gas inlet, the gas outlet and the reaction chamber are configured to operate:
    in a first mode of operation, wherein the precursor solution is continuously guided though the reaction chamber and a power of the radiation acting on the precursor solution is held at a constant level such that a concentration of generated nitric oxide in the carrier gas is substantially constant;
    in a second mode of operation, wherein the precursor solution is pulsed through the reaction chamber, and the power of the radiation is correspondingly pulsed to the constant level, such that a concentration of nitric oxide in the carrier gas generated from an individual second mode pulse of precursor solution decreases with time; and
    in a third mode of operation, wherein the precursor solution is pulsed through the reaction chamber, and the power of the radiation is correspondingly increased over time for an individual third mode pulse of precursor solution, such that the concentration of nitric oxide in the carrier gas generated from the individual third mode pulse of precursor solution is constant over time.

9. Apparatus according to claim 8, wherein a gas reservoir is provided downstream from the reaction chamber.

10. Apparatus according to claim 8, wherein a recirculation loop is provided, for guiding the reacted solution back to the first reservoir.

11. Apparatus according to claim 10, wherein a third reservoir for receiving precursor solution is provided in fluid communication with the recirculation loop, the first reservoir, and/or the second reservoir.

12. Apparatus according to claim 8, wherein a nitric oxide detector is provided downstream from the reaction chamber.

13. Apparatus according to claim 8, wherein a control unit is provided for adjusting at least one reaction parameter according to the nitric oxide concentration downstream from the reaction chamber.

* * * * *